(12) United States Patent
Benjamin et al.

(10) Patent No.: US 8,162,975 B2
(45) Date of Patent: Apr. 24, 2012

(54) SYSTEMS AND METHODS FOR CLOSING A PERCUTANEOUS VASCULAR PUNCTURE

(75) Inventors: Thierry Benjamin, Lowell, MA (US); Matthew Spurchise, Peabody, MA (US); Juan-Pablo Mas, Indianapolis, IN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 350 days.

(21) Appl. No.: 12/437,652

(22) Filed: May 8, 2009

(65) Prior Publication Data
US 2010/0286725 A1 Nov. 11, 2010

(51) Int. Cl.
*A61B 17/08* (2006.01)
(52) U.S. Cl. ........................................ 606/213; 606/153
(58) Field of Classification Search .................. 606/213, 606/215, 216, 221; 623/1.11, 1.12; 604/102.01, 604/103.05, 117, 158, 163, 168.01
See application file for complete search history.

(56) References Cited

U.S. PATENT DOCUMENTS

| 4,581,017 | A | | 4/1986 | Sahota | |
|---|---|---|---|---|---|
| 4,787,899 | A | * | 11/1988 | Lazarus | 623/1.11 |
| 5,151,105 | A | | 9/1992 | Kwan-Gett | |
| 5,282,827 | A | | 2/1994 | Kensey et al. | |
| 5,522,882 | A | | 6/1996 | Gaterud et al. | |
| 5,891,154 | A | * | 4/1999 | Loeffler | 623/1.11 |
| 6,004,347 | A | * | 12/1999 | McNamara et al. | 623/23.64 |
| 6,712,842 | B1 | * | 3/2004 | Gifford et al. | 623/1.13 |
| 7,074,232 | B2 | | 7/2006 | Kanner et al. | |
| 7,175,651 | B2 | | 2/2007 | Kerr | |
| 7,892,246 | B2 | | 2/2011 | Akin et al. | |
| 2006/0287714 | A1 | * | 12/2006 | Erbel et al. | 623/1.44 |
| 2007/0198078 | A1 | | 8/2007 | Berra et al. | |
| 2008/0058918 | A1 | * | 3/2008 | Watson | 623/1.13 |

* cited by examiner

*Primary Examiner* — Tuan Nguyen
*Assistant Examiner* — Thomas McEvoy

(57) ABSTRACT

A system and method for closing a percutaneous vessel puncture at the conclusion of a vascular catheterization procedure includes placement of an intravascular closure device having a radially and axially expandable tubular membrane and a radially expandable anchor at the distal end of the membrane. The closure device is placed, by a delivery catheter extending through the puncture site, with its anchor radially expanded in a location upstream of the puncture site to enable the force of a patient's blood flow to deploy the tubular membrane to a proximally extended configuration closing the puncture from within the vessel.

8 Claims, 5 Drawing Sheets

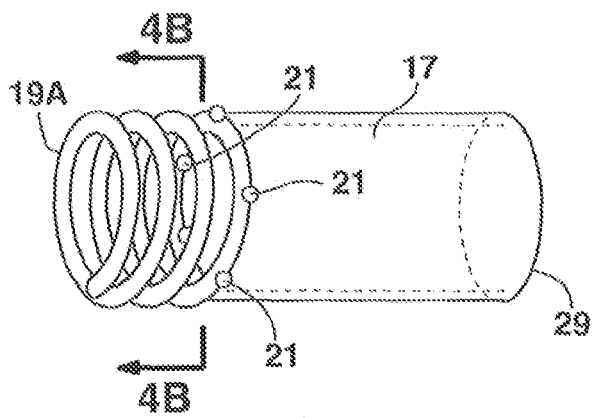
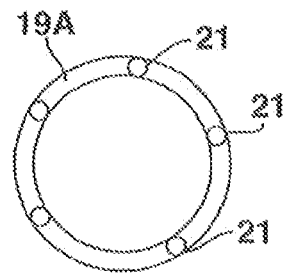
FIG. 4A  FIG. 4B
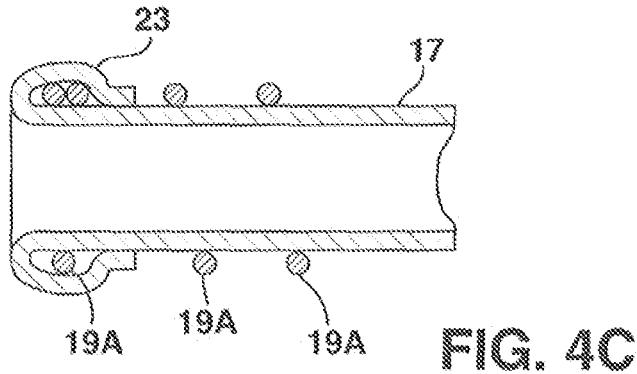
FIG. 4C
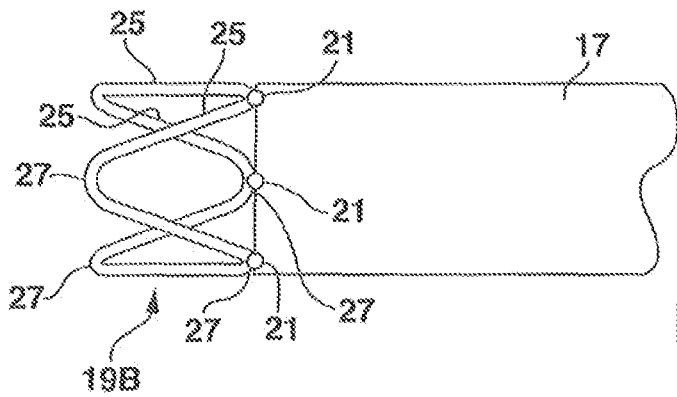
FIG. 4D
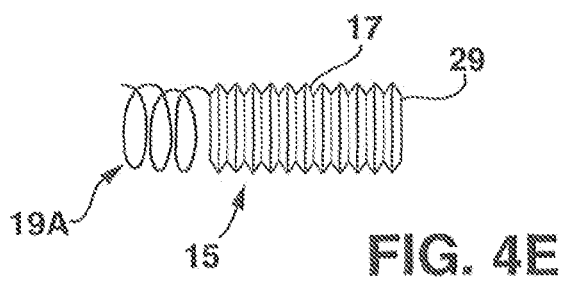
FIG. 4E

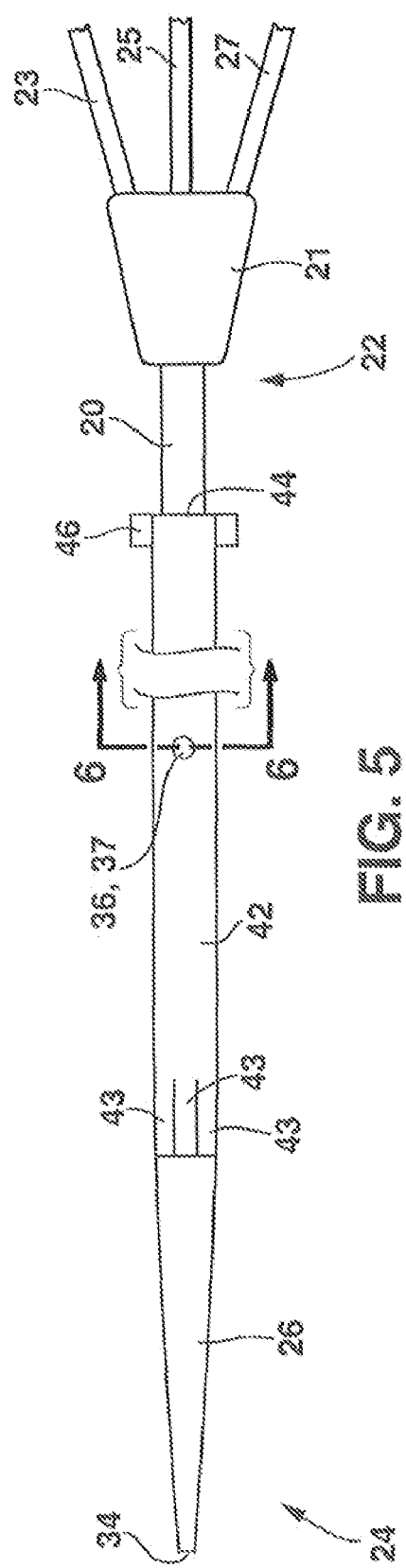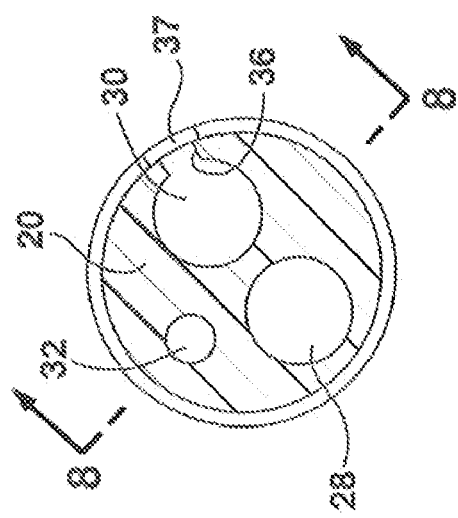

SYSTEMS AND METHODS FOR CLOSING A PERCUTANEOUS VASCULAR PUNCTURE

FIELD OF THE INVENTION

The invention rotates to systems and techniques for closing a percutaneous puncture in a blood vessel at the conclusion of an intravascular catheterization procedure.

BACKGROUND

Various cardiovascular procedures, such as angioplasty and stent placement, among others, are performed by inserting into and manipulating within a patient's vasculature, wires and catheters adapted to perform those procedures. In coronary and other such intravascular interventional procedures access to the vasculature typically is percutaneous, often through the femoral artery, involving insertion of a needle in the region of the groin to form a track through subcutaneous tissue and to puncture and create an arteriotomy in the artery. A guide wire then is advanced through the needle and into the femoral artery. The needle then is removed and a dilator carrying an introducer sheath then is advanced over the guidewire, along the needle track and into the femoral artery. The dilator enlarges the track through the tissue and widens a puncture in the vessel so that it may receive the introducer sheath, subsequent catheters and the like. With the introducer sheath having been advanced into the vessel, the dilator is removed leaving the introducer sheath in place. The guidewire and introducer sheath serve as guides to provide access into the femoral artery, through the arteriotomy, for catheters or other instrumentalities in order to perform the selected procedure within the patient's vasculature.

After the intravascular procedure has been completed, the procedural devices are removed and the arteriotomy must be closed. A number of techniques are known to facilitate closure and healing of the arteriotomy. These include application of pressure at the puncture site, often for a relatively extended length of time until hemostasis is self-sustaining, or the use of biological adhesives or plugs adapted to seal the arteriotomy, or the use of staples or clips. Some closure systems include a patch in an external position covering the arteriotomy and connected by a suture that extends through the puncture to an internal anchor element that spans the opening. Some closure systems include an arrangement to engage the artery to temporarily draw the edges of the arteriotomy together while a filial closure device, such as a staple, sutures, adhesives or other means may be used to effect the permanent closure of the arteriotomy. Some closure systems include a tubular guiding sheath that is percutaneously positioned through the enlarged needle track with a distal outlet opening of the guiding sheath disposed immediately adjacent the arteriotomy. With the sheaths so positioned, closure device can be advanced through the sheath to apply its closure element or procedure to the region of the arteriotomy to close it. In order for such a sheath-based system to be effective, it is important that the distal end of the sheath be stabilized in a fixed position relative to the vascular puncture. After the closure device has performed its function and hemostasis has been achieved, the sheath and other elements of the closure system are removed.

A challenge associated with most known vascular closure devices (VCDs) is locating the exterior surface of the vessel wail and distinguishing that surface from the surrounding subcutaneous tissue so that the closure device can be applied accurately with respect to that exterior surface. Errors in accurately determining the exterior surface of the vessel wall can result in hematoma if the VCD is deployed too far away from the vessel wall, or can result in embolization if the VCD is unintentionally deployed within the vessel lumen. It would be desirable to provide a system that can promptly and effectively achieve permanent hemostasis at a percutaneous vascular puncture without requiring the clinician to accurately locate the exterior surface of the vessel wall at an arteriotomy.

SUMMARY OF THE INVENTION

The invention provides a closure system and methods for closing a puncture in a blood vessel, such as an arteriotomy. A delivery catheter of the system carries a tubular closure device in a radially compressed mounted configuration into the vessel lumen and deploys it to its expanded tubular configuration to lie against the inner luminal wall and cover the puncture from the interior of the vessel. The tubular closure device comprises a flexible membrane having leading and trailing ends and an expandable anchor connected to the leading end thereof. The system also includes ah outer sheath that covers and maintains the closure device, in its compact mounted configuration during delivery on the catheter. When the catheter is positioned to locate the leading end of the sealing device at a pre-determined position in the vessel lumen upstream of the vascular puncture, the sheath is retracted and the closure device is expanded at that location. With the anchor expanded to a secure position in the vessel, upstream of the vessel puncture, the delivery catheter, sheath and guidewire are removed. Blood flow through the membrane extends the membrane downstream beyond the puncture and maintains it in its tubular shape, lining the luminal, surface of the vessel wall and covering the puncture from within the vessel to provide hemostasis. The closure device may be made from a bioabsorbable material selected to degrade after passage of time sufficient to allow the puncture to heal naturally.

DESCRIPTION OF THE DRAWINGS

The accompanying drawings are not intended to be in scale and in some cases are in exaggerated scale for ease of explanation and illustration.

FIG. 4A is a diagrammatic illustration of a closure device in which the anchor is in the form of a helical coil with die distal end of the tubular membrane attached to the coil;

FIG. 4B is an illustration of the points of attachment of the membrane to the coil as seen along the line 4B-4B of FIG. 4A;

FIG. 4C is a diagrammatic longitudinal sectional illustration of another manner of attaching the tubular membrane to an expandable coil;

FIG. 4D is an illustration of another type of anchor attached to a tubular member;

FIG. 4E is a diagrammatic illustration of the vascular closure device in its low profile, axially compacted configuration;

FIG. 5 is a fragmented illustration of the puncture closure delivery catheter and sheath;

FIG. 6 is a sectional view of the delivery catheter and sheath as seen along the line 6-6 of FIG. 5;

DESCRIPTION OF THE ILLUSTRATIVE EMBODIMENTS

In the description of the invention, "proximal," "rearward" and "trailing" will refer to a direction away from the patient, that is, toward the operator of the device, and "distal," "forward" and "leading" will refer to the opposite direction, away from the clinician, and toward the patient.

Figure 1:
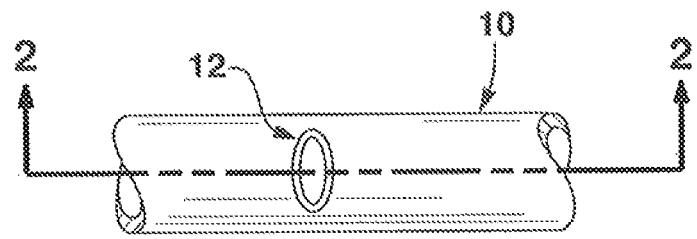
FIG. 1 is a diagrammatic plan illustration of a portion of a blood vessel with a vascular puncture.
Figure 2:
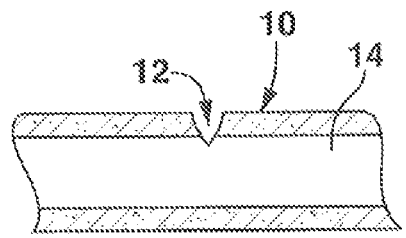
FIG. 2 is a diagrammatic illustration, in section, of the blood vessel as seen along the line 2-2 of FIG. 1.
Figure 3:
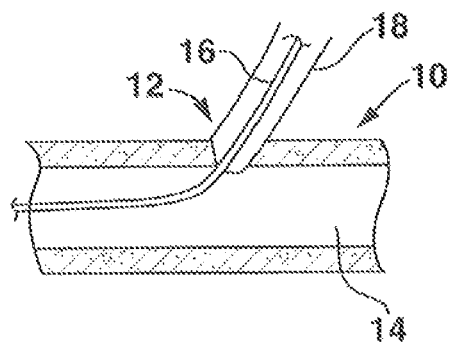
FIG. 3 is a diagrammatic illustration of a blood vessel with a guidewire extending through a needle track (in phantom) in subcutaneous tissue, the vessel puncture and into the lumen of the vessel after an intravascular procedure has been completed but before the puncture has been closed.

FIGS. 1-3 illustrate, diagrammatically, a segment of a blood vessel 10 (e.g., an artery) that has been punctured by a needle (not shown) to form an arteriotomy 12 through which various wires, catheters and the like may be advanced and guided into the lumen 14 of the vessel in order to perform any of a variety of well-known intravascular procedures. As shown in FIG. 1, the typical shape of the resulting puncture in an artery is in the form of a slit that extends in a circumferential direction, resulting from the muscle structure of the artery in which the muscle fibers extend generally circumferentially. Typically, the needle puncture that initiates the arteriotomy is followed by subsequent, larger diameter instruments that progressively dilate the dimensions of arteriotomy 12 to be able to accept the larger intravascular devices. FIG. 3 illustrates the vessel and needle track 18 (shown in phantom) through subcutaneous tissue by the puncture needle and with an indwelling guidewire 16 extending through the track and into the vessel lumen 14, as may remain after the intravascular procedures have been completed and the last of the catheters and introducer sheath have been removed from the patient. At this point in the procedure, it is necessary to close arteriotomy 12. FIGS. 1-3 do not illustrate elements of the invention, but are intended to show an exemplary clinical environment in which the invention may be used.

Figure 4:
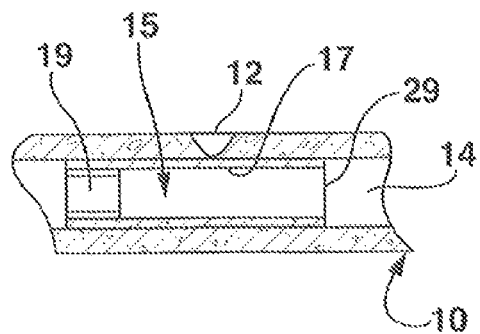
FIG. 4 is a diagrammatic illustration of the closure device in its fully deployed configuration, with the tubular closure membrane having been extended longitudinally and in a downstream direction to cover the puncture from the interior of the vessel.

As illustrated prophetically in FIG. 4, the present invention closes arteriotomy 12 by lining the interior of blood vessel 10 with a closure device 15 that, when deployed, has a tubular membrane 17 that lines the inner luminal surface of vessel 10 and covers puncture 12 from within the artery. The device is inserted through arteriotomy 12 by a delivery device described below. Closure device 15 includes an anchor 19 at its distal, leading end with the tubular membrane 17 extending proximally from and trailing the anchor when deployed. The device is delivered in a low-profile mounted configuration that is both radially and axially compacted and is deployed by causing it to expand radially and axially within the vessel lumen. When deployed, as shown in FIG. 4, the trailing portion of the membrane is expanded radially and is axially expanded and maintained in an open tubular configuration by forces exerted by the patient's blood flow. Liner 17 serves to cover arteriotomy 12 from within to enable the arteriotomy to heal naturally while maintaining hemostasis. Closure device 15 may be formed from bioabsorbable materials selected to be absorbed by the body after a sufficient time has passed to permit healing of the vessel puncture site. Suitable bioabsorbable materials may include poly-alpha-hydroxy adds such as polyglycolic acid (PGA), polylactic acid, copolymers of lactic and glycolic acids, and such polymers copolymerized with ε-caprolactone or trimethylene carbonate. Suffer bioabsorbable materials may be utilized as fine fibers in braided tubes or non-oriented tubular fibrous mats wherein the porosity of liner 17 is small to begin with, and which will quickly be sealed by clotting. More flexible materials, e.g. glycolide copolymers, may be utilized in solid tubular form.

The anchor 19 may take any of a number of known configurations, such as a radially expandable helical coil or a radially expandable stent-like device. FIGS. 4A and 4B illustrate, diagrammatically, a radially expandable anchor 19A in the form of a helical coil that may be formed from any of a variety of biocompatible materials (e.g., stainless steel, nitinol) capable of retaining a radially expanded configuration within a vessel lumen. The distal end of tubular membrane 17 may be attached, as by adhesive or thermal bonding to anchor 19A directly at a plurality of locations 21 that will allow both anchor 19A and the distal end of the membrane 17 to expand radially from their low profile configuration on the delivery catheter to an expanded, deployed condition in secure engagement with the inner luminal surface of the vessel (FIG. 4). Other modes of attachment of the tubular membrane to the anchor 19A may be employed, such as by passing the distal end of the membrane through the anchor and folding back a margin 23 of the distal end of the membrane as shown in FIG. 4C. Everted margin 23 may be attached to the adjacent portions of the tubular membrane 17 in a manner that defines a circular passageway through which a loop of the helical coil of the anchor 19A may expand radially from a low profile to a deployed diameter.

FIG. 4D illustrates another type of anchor 19B, similar to one or more modules of a zigzag type of stent known to those in the art. This anchor 19B is formed from a wire-like structure that defines alternating struts 25 joined end-to-end or formed into bends 27. In this embodiment, the distal end of tubular membrane 17 may be attached at a number of individual points 21, such as at the bends 27 of the zigzag configuration. The tubular membranes 17, in each case, are formed from a thin biodegradable film. The anchors, however, if formed from a metal, may remain implanted in the artery after the puncture has healed and the tubular membrane has been absorbed. The anchors also may be formed from a biodegradable polymer capable of expansion to a radially expanded size that will retain itself within the vessel during deployment and subsequent degradation.

The trailing portion of membrane 17 is compacted axially, in somewhat of an accordion fashion, as suggested diagrammatically in FIG. 4E, that will permit the compacted closure device to be deployed in its entirety upstream of the arteriotomy and will permit the axial expansion of the membrane under the influence of blood flow and blood pressure after the delivery device has been withdrawn.

Figure 7:
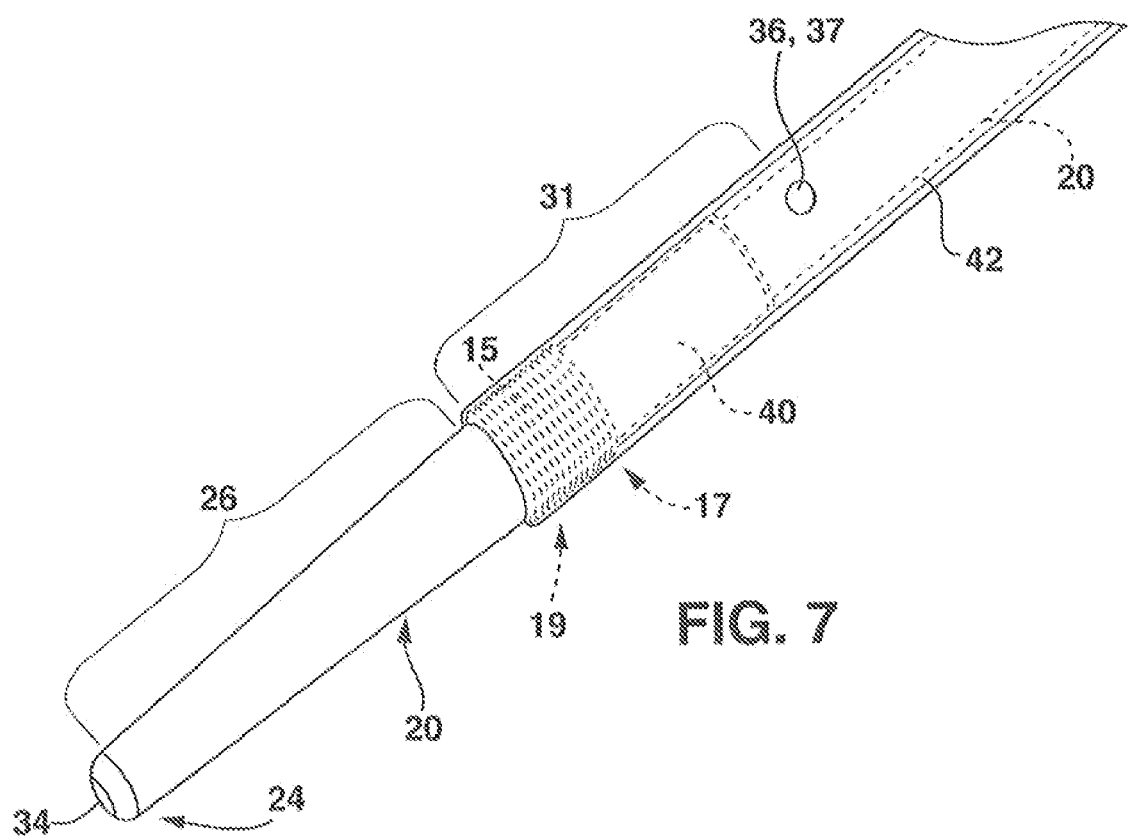
FIG. 7 is a diagrammatic illustration of the distal end of the delivery device showing a portion of a balloon expansion element and the closure device.
Figure 8:
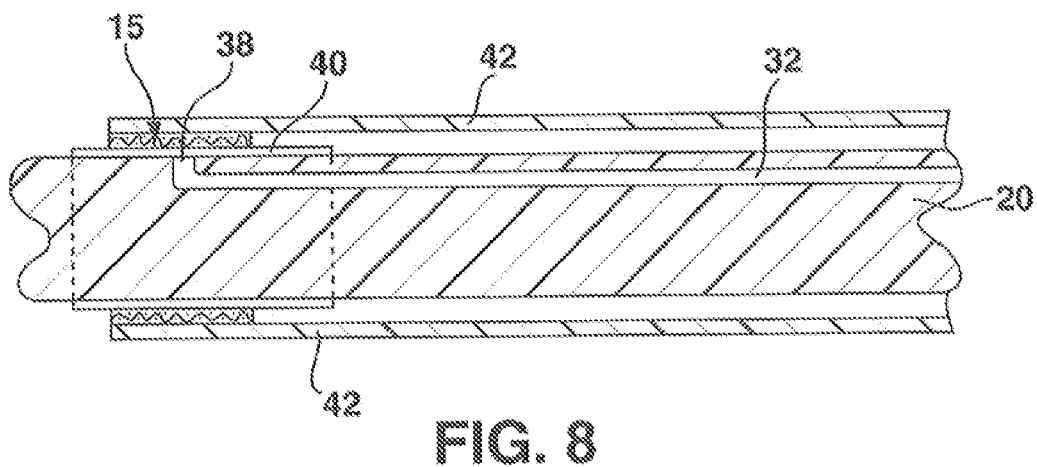
FIG. 8 is a longitudinal sectional elevation of a portion of the delivery device of FIG. 7 as seen along the line 8-8 of FIG. 6.

FIGS. 5-8 depict, somewhat diagrammatically, an illustrative embodiment of a delivery device for use in the practice of the invention. The device includes a catheter 20 that may be formed as an elongate flexible shaft, as by extrusion, from any of a variety of polymers commonly used in the construction of catheter shafts, such as PEBAX® polyethylene block amide co-polymer from ARKEMA, Philadelphia, Pa. Catheter 20 has a proximal end 22 and a distal end 24, the distalmost portion of the shaft having a taper 26 to facilitate passage along subcutaneous needle track 18 and through vascular puncture 12. In the illustrative embodiment, catheter 20 has three lumens, including a guidewire lumen 28, a blood marking lumen 30 and a balloon inflation lumen 32 (FIG. 6). Guidewire lumen 28 extends from proximal end 22 of the catheter and terminates in a distal opening 34 at distal end 24 of catheter 20. Blood marking lumen 30 extends from the proximal end 22 of the catheter and communicates with the exterior of the catheter through a distal blood marking port 36 that opens through the sidewall of catheter 20 and an outer port 37 formed in an outer sheath, described below. Inflation lumen 32 extends from the proximal end 22 of the catheter and communicates with a distal port 38 extending through the sidewall of the catheter (FIG. 8). The proximal end of catheter 20 may include a fitting 21 that may be molded directly onto the shaft and serves to secure several tubes 23,25,27 in communication, respectively, with inflation lumen 32, guidewire lumen 28 and blood marking lumen 30 that extend through catheter 20.

The delivery device also includes a tubular sheath 42 that is slidably disposed on catheter 20. The distal portion of the sheath 42 overlies and contains closure device 15 and balloon 40, maintaining them in a low profile during delivery. Sheath 42 has a length that is less than that of catheter 20 and has a proximal end 44 that allows the sheath to be withdrawn proximally over catheter 20 to expose closure device 15 and allow balloon 40 to expand and deploy closure device 15. Optionally, the distal end of sheath 42 may have slits or weakened lines that define separable distal tabs 43 in the case where balloon 40 is expanded without having first fully retracted sheath 42 therefrom.

As shown in FIGS. 7 and 8, catheter 20 includes an expansion element, here an expandable balloon 40, secured to and overlying distal inflation port 38 of the catheter 20, enabling the balloon to be inflated with fluid through inflation lumen 32. Balloon 40 may be formed in a manner and from materials, such as PET, well known to those skilled in the art, and may be attached to the shaft, also by means well known in the art, such as adhesive. Closure device 15 is mounted about catheter 20 so that anchor 19 at the leading end of the closure device is disposed about the deflated balloon in readiness to be expanded when balloon 40 is inflated. Tubular membrane 17 has an axially contracted mounted length when mounted about catheter 20, and may optionally be mounted about balloon 40.

When sheath 42 is in its distal position with its distal, end overlying closure device 15, the distal blood marking port 37 of the sheath is in registry with the distal blood marking port 36 of the catheter 20, in readiness to direct blood through the aligned ports 36,37 into blood marking lumen 30. When the delivery device has been advanced into the blood vessel to place the distal blood marking ports 36, 37 within the vessel, blood flows through the blood marking ports and that catheter position is signaled to the clinician by the visible presence of blood in proximal blood marking tube 27. The distance 31 between anchor 19 of closure device 15 and the distal blood marking ports 36, 37 is fixed at a predetermined dimension to provide an indication to the clinician of the location of closure device 15 relative to puncture wound 12 when blood is first observed in blood marking lumen 27. The delivery device should be advanced distally in the vessel to assure that the entire closure device, including the proximal end of the axially compacted tubular membrane 17, is within the vessel, and distally beyond the puncture. The placement of the anchor at a proper location in the vessel is facilitated by the blood marking indication arrangement. The tubular membrane 17 is dimensioned to have an expanded length, when deployed, greater than the distance 31 between the distal blood marking ports 36, 37 and the anchor 19 so that, when deployed, tubular membrane 17 will be able to be extended downstream sufficiently to cover the puncture 12.

Sheath 42, which is shorter than catheter 20, may be provided with a gripping member, shown diagrammatically at 46, or other mechanism to facilitate its retraction from a distal delivery position to its retracted deployment position. The length of the retractable sheath preferably is such as to fully uncover the membrane 17 when the sheath is retracted.

Figure 9A:
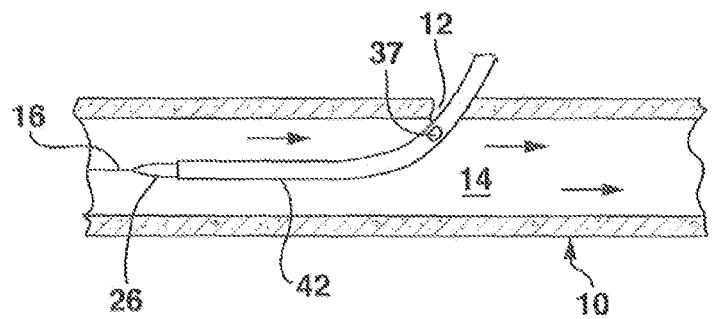
FIG. 9A is a diagrammatic illustration of a vascular puncture closure system in accordance with the invention having been advanced over a guidewire, through the vascular puncture and shown with the distal blood marking port within the vessel to place the closure device at a selected location upstream of the puncture site.
Figure 9B:
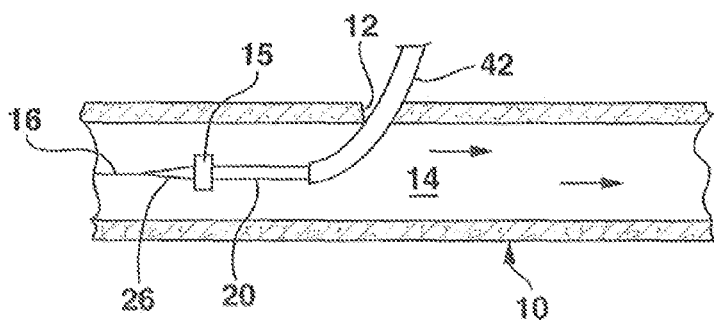
FIG. 9B is a diagrammatic illustration of the system in the vessel with the sheath retracted to expose the closure device and balloon.
Figure 9C:
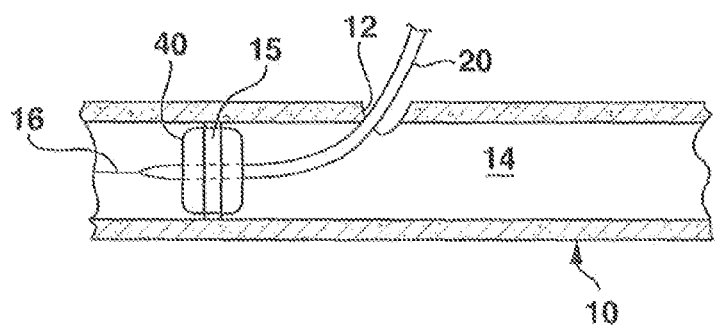
FIG. 9C is a diagrammatic illustration of the system with the balloon inflated to expand the closure device at a location upstream of the puncture.
Figure 9D:
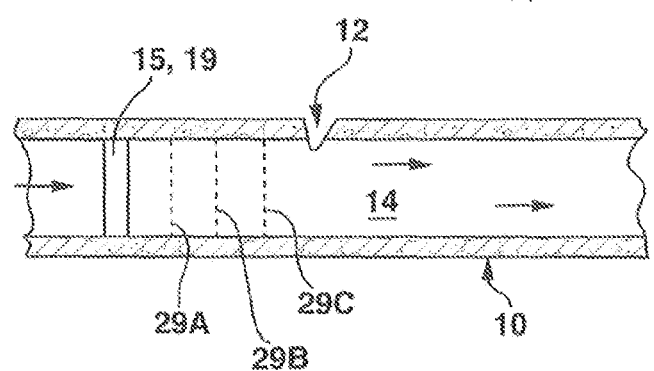
FIG. 9D is a diagrammatic illustration of the vessel after the delivery catheter has placed the closure device and the delivery catheter has been removed.

The closure system is used in a manner illustrated prophetically in FIGS. 4, and 9A-9D. After the vascular procedure has been completed and the associated interventional catheters have been removed, leaving only the indwelling guidewire 16 in place (FIG. 3), the closure system containing the closure device is backloaded onto the proximal end of the externally accessible guidewire 16. The closure system, guided by the guidewire 16, is advanced through the vessel puncture 12 until the clinician observes the presence of blood at the proximal blood marking tube or port 27 (FIG. 9A). That signals the clinician that the device has been advanced to position the closure device 15 distally of the vascular puncture 12 and at a location to allow the deployed membrane to cover the puncture. The closure system may be partially withdrawn and advanced repeatedly, if necessary, in order for the clinician to confirm that blood marking port 37 is located just within vessel lumen 14 at arteriotomy 12. Sheath 42 then is retracted proximally to expose closure device 15 and balloon 40 (FIG. 9B). Balloon 40 then may be expanded by directing pressurized fluid through inflation lumen 32 (FIG. 9C). Closure device 15 is expanded radially by balloon 40 into firm engagement with the inner luminal wall of the vessel 10. Balloon 40 then is deflated and the delivery device and the guidewire are removed through the puncture 12, leaving the radially expanded, closure device 15 anchored within the blood vessel lumen (FIG. 9D). As closure device 15 is subjected to the blood flow in the vessel (see arrows), the trailing portion 29 of tubular membrane 17 extends of unfurls progressively, as shown in successive positions 29A, 29B and 29C. Finally, tubular member 17 longitudinally opens fully in a downstream direction to cover the interior of the vessel wall and obstruct the vessel puncture 12 (FIG. 4). Anchor 19 and membrane 17 may be formed from bioabsorbable materials that, over time, allow the puncture wound to heal naturally.

It should be understood that although the foregoing illustrative embodiments are described in the context of a balloon expansion device, the anchors may be formed to have self-expanding characteristics such that they will self-expand in response to their inherent resilience when the sheath is retracted. A self-expanding anchor may be of the coiled or zigzag forms described above, or it may be formed of braided filaments using the same anchor materials described above. In such an embodiment, the sheath maintains the self-expanding anchor in its low profile condition and in readiness to expand when released by retraction of the sheath.

The dimensions of a device in accordance with the invention will, of course, depend on the size of the vessel with which it is to be used. For example, in the case of a puncture in the femoral artery, sheath 42 of the delivery device may have an outer diameter of the order of about 0.033 inch. The anchor may be of the order of about 0.070 inch outer diameter when in its low profile configuration. It should be expandable up to about 0.350 inch, to be usable in a vessel having an inner diameter of up to about 8 millimeters.

It should be understood that the foregoing description of the invention is intended merely to be illustrative and that other embodiments and equivalents may be employed within the scope of the invention.

What is claimed is:

1. A system for closing a percutaneous puncture in a blood vessel, the system including:
  a delivery catheter comprising an elongate flexible shaft having a proximal end and a tapered portion at a distal end and a single blood marking side port spaced proximally of the shaft taper and being in fluid communication with only the shaft proximal end via a blood marking lumen extending axially through the shaft, the catheter further comprising a balloon affixed about the shaft between the shaft tapered portion and the blood marking side port and being in fluid communication with the shaft proximal end via an inflation lumen extending axially through the shaft;
  a closure device mounted about the balloon, the closure device comprising a tubular membrane having open proximal and distal ends and an axially contracted mounted length shorter than an axially expanded length, the closure device further comprising a radially expandable tubular anchor attached to the distal end of the membrane such that a trailing portion of the membrane extends proximally from the anchor when the closure device is in an axially expanded configuration, the closure device adapted for transformation between:
    a mounted configuration wherein the anchor and the membrane are radially compressed about the shaft and the length of the membrane is the mounted length;
    a radially expanded configuration wherein the anchor and the membrane are radially expanded and the length of the membrane is the mounted length; and
    the axially expanded configuration wherein the anchor and the membrane are radially expanded and the length of the membrane is the axially expanded length;
  a tubular sheath having an initial position disposed about the shaft and the closure device, the sheath having a blood marking port in registry with the blood marking port of the shaft when the sheath is in its initial position, the sheath being retractable from its initial position proximally to expose the balloon and the anchor of the closure device; and
  wherein the balloon is spaced from the catheter blood marking port by a distance less than the axially expanded length of the membrane, and the balloon is inflatable to transform the closure device from the mounted configuration to the radially expanded configuration; and
  wherein the membrane is sufficiently flexible such that the closure device is transformable from the radially expanded configuration to the axially expanded configuration under the influence of a patient's blood flow therethrough.

2. The system of claim 1 further comprising a guidewire lumen extending from the shaft proximal end to an axial opening in the shaft distal end.

3. The system of claim 1 wherein the anchor is expandable radially from a low profile to an expanded profile adapted to firmly engage an inner luminal surface of the vessel.

4. The system of claim 3 wherein the membrane of the closure device is expandable radially from a low profile to an expanded profile.

5. The system of claim 1 wherein at least a portion of the closure device is biodegradable.

6. The system of claim 1 wherein the anchor comprises a helical coil and wherein the distal end of the membrane is attached to the coil at a plurality of circumferentially spaced locations whereby both the anchor and the distal end of the flexible tube can expand together radially to transform the closure device from the mounted configuration to the radially expanded configuration.

7. The system of claim 6 wherein a margin at the distal end of the membrane is everted about a loop of the coil and is secured to a more proximal portion of the membrane to define a circular passageway containing a loop of the anchor.

8. The system of claim 1 wherein the anchor comprises an expandable zigzag ring and wherein the distal end of the membrane is attached to the zigzag ring at a plurality of circumferentially spaced locations whereby both the anchor and the distal end of the flexible tube can expand together radially to transform the closure device from the mounted configuration to the radially expanded configuration.

* * * * *